US012213748B2

(12) United States Patent
Dahan et al.

(10) Patent No.: US 12,213,748 B2
(45) Date of Patent: Feb. 4, 2025

(54) SYSTEMS AND METHODS FOR REGISTERING ONE OR MORE ANATOMICAL ELEMENTS

(71) Applicant: Mazor Robotics Ltd., Caesarea (IL)

(72) Inventors: Ofir Dahan, Haifa (IL); Nir Ofer, Tel Aviv-Jaffa (IL); Yair S. Schwartz, Herzliya (IL); Gal Barazani, Haifa (IL); Maor Sviri, Ramat Gan (IL); Itay Jerby, Netanya (IL)

(73) Assignee: Mazor Robotics Ltd., Caesarea (IL)

( * ) Notice: Subject to any disclaimer, the term of this patent is extended or adjusted under 35 U.S.C. 154(b) by 270 days.

(21) Appl. No.: 17/591,863

(22) Filed: Feb. 3, 2022

(65) Prior Publication Data

US 2023/0240755 A1     Aug. 3, 2023

(51) Int. Cl.
*A61B 34/20*     (2016.01)
*A61B 34/30*     (2016.01)
(Continued)

(52) U.S. Cl.
CPC .............. *A61B 34/20* (2016.02); *A61B 34/30* (2016.02); *A61B 90/39* (2016.02); *G06T 7/0012* (2013.01); *G06T 7/11* (2017.01); *G06T 7/38* (2017.01); *G16H 30/20* (2018.01); *A61B 2034/2065* (2016.02); *A61B 2034/2068* (2016.02); *A61B 2090/3916* (2016.02); *A61B 2090/3945* (2016.02); *A61B 2090/3954* (2016.02); *A61B 2090/3966* (2016.02); *A61B 2090/3979* (2016.02); *A61B 2090/3983* (2016.02);
(Continued)

(58) Field of Classification Search
CPC . A61B 90/39; A61B 2090/3916; A61B 34/20; A61B 2034/2065; A61B 2034/256; A61B 2090/376
See application file for complete search history.

(56) References Cited

U.S. PATENT DOCUMENTS

2019/0090955 A1    3/2019   Singh et al.
2020/0405397 A1   12/2020   Liu et al.
(Continued)

FOREIGN PATENT DOCUMENTS

EP          4104786       12/2022

OTHER PUBLICATIONS

International Search Report and Written Opinion for International (PCT) Patent Application No. PCT/IL2023/050078, dated Apr. 24, 2023, 14 pages.

*Primary Examiner* — Amelie R Davis
(74) *Attorney, Agent, or Firm* — Sheridan Ross P.C.

(57) ABSTRACT

Systems and methods for registering one or more anatomical elements are provided. The system may comprise an imaging device and a navigation system configured to track a pose of a marker coupled to an object and configured to identify the marker. A first image may be received from a surgical plan. Pose information describing the pose of the marker and a marker identification of the marker may be obtained from the navigation system. An object identification based on the marker identification may be retrieved from a database. Image data of a second image depicting an anatomical element and the object may be obtained from the imaging device. The image data, the pose information, and the object identification may be input into a registration model. The registration model may be configured to register the anatomical element to the first image based on the pose information and the object identification.

16 Claims, 6 Drawing Sheets

(51) Int. Cl.
    *A61B 90/00*  (2016.01)
    *G06T 7/00*   (2017.01)
    *G06T 7/11*   (2017.01)
    *G06T 7/38*   (2017.01)
    *G16H 30/20*  (2018.01)

(52) U.S. Cl.
    CPC ............... *G06T 2207/10116* (2013.01); *G06T 2207/30012* (2013.01)

(56) References Cited

U.S. PATENT DOCUMENTS

| | | |
|---|---|---|
| 2022/0008141 A1 | 1/2022 | Chopra et al. |
| 2022/0031370 A1 | 2/2022 | Zehavi et al. |

SYSTEMS AND METHODS FOR REGISTERING ONE OR MORE ANATOMICAL ELEMENTS

BACKGROUND

The present disclosure is generally directed to registration, and relates more particularly to registering one or more anatomical elements that may be partially blocked by an object.

Navigation systems may assist a surgeon or other medical provider in providing navigation to the surgeon and/or a robotic system to carry out a surgical procedure. Registration may occur prior to a start of a surgical procedure to correlate actual patient anatomy in the surgical space to a preoperative image or three-dimensional representation of the patient anatomy.

BRIEF SUMMARY

Example aspects of the present disclosure include:

A system for registering one or more anatomical elements according to at least one embodiment of the present disclosure comprises an imaging device; a navigation system configured to track a pose of a marker coupled to an object and further configured to identify the marker; a processor; and a memory storing data for processing by the processor, the data, when processed, causing the processor to: receive a first image from a surgical plan; obtain, from the navigation system, pose information describing the pose of the marker and a marker identification of the marker; retrieve, from a database, an object identification based on the marker identification, wherein the database stores marker identification information for each of a plurality of markers and corresponding object identification information for each of an associated plurality of objects; obtain, from the imaging device, image data of a second image depicting an anatomical element and the object; and input the image data, the pose information, and the object identification into a registration model, the registration model configured to register the anatomical element to the first image based on the pose information and the object identification.

Any of the aspects herein, wherein the memory stores further data for processing by the processor that, when processed, causes the processor to: receive from the registration model, a registered anatomical element Any of the aspects herein, wherein the memory stores further data for processing by the processor that, when processed, causes the processor to: input the image data, the pose information, and the object identification into an image processing model, the image processing model configured to process the image data to identify the anatomical element and the object in the image data; and receive from the image processing model, an identified anatomical element and an identified object.

Any of the aspects herein, wherein the registration model uses image processing to identify the object within the image data based on the pose information and the object identification and the registration model flags the object for non-use by the registration.

Any of the aspects herein, wherein the image data includes a portion of the anatomical element, the anatomical element partially blocked by the object, and wherein the registration model registers the anatomical element based on the portion depicted.

Any of the aspects herein, wherein identifying the object within the image data comprises identifying pixels of the image data corresponding to the object and wherein the registration model flags the identified pixels for non-use by the registration.

Any of the aspects herein, wherein the memory stores further data for processing by the processor that, when processed, causes the processor to: retrieve dimensions of the object from the database based on the object identification, wherein the pixels are identified based on the pose information and the dimensions of the object.

Any of the aspects herein, wherein the marker comprises at least one of an optical marker, a magnetic marker, a light emitting diode, or an infrared light emitting diode.

Any of the aspects herein, wherein the object is at least one of a radiopaque bone mount, a surgical implant, and a surgical tool.

Any of the aspects herein, wherein the first image is a three-dimensional representation of the anatomical element and the second image is a two-dimensional representation of the anatomical element.

Any of the aspects herein, wherein the imaging device uses X-Ray imaging.

A system for registering one or more anatomical elements according to at least one embodiment of the present disclosure comprises a navigation system configured to track a pose of a marker and identify the marker; a database configured to store marker identification for each of a plurality of markers and corresponding object identification for each of a plurality of objects; a processor; and a memory storing data for processing by the processor, the data, when processed, causing the processor to: receive a first image from a surgical plan; obtain, from the navigation system, pose information describing the pose of the maker and a marker identification of the marker; retrieve, from the database, an object identification based on the marker identification; receive image data of a second image depicting an anatomical element and the object; input the image data, the pose information, and the object identification into a registration model, the registration model configured to register the anatomical element to the first image based on the pose information and the object identification; and receive from the registration model, a registered anatomical element.

Any of the aspects herein, wherein the memory stores further data for processing by the processor that, when processed, causes the processor to: input the image data, the pose information, and the object identification into a segmentation model, the segmentation model configured to segment the image data to identify the anatomical element and the object in the image data; and receive from the segmentation model, an identified anatomical element and an identified object.

Any of the aspects herein, wherein the registration model identifies the object within the image data based on the pose information and the object identification and flags the object for non-use by the registration.

Any of the aspects herein, wherein the image data depicts a portion of the anatomical element, the anatomical element partially blocked by the object, and wherein the registration model does not use the image data depicting the object when identifying and registering the anatomical element based on the portion depicted.

Any of the aspects herein, wherein identifying the object within the image data comprises identifying pixels of the image data corresponding to the object and flagging the identified pixels for non-use by the registration.

Any of the aspects herein, wherein the memory stores further data for processing by the processor that, when processed, causes the processor to: retrieve dimensions of the object from the database based on the object identification, wherein the pixels are identified based on the pose information and the dimensions of the object.

Any of the aspects herein, wherein the marker comprises at least one of an optical marker, a magnetic marker, a light emitting diode, or an infrared light emitting diode.

Any of the aspects herein, wherein the object is at least one of a radiopaque bone mount, a surgical implant, and a surgical tool.

A system for registering one or more anatomical elements according to at least one embodiment of the present disclosure comprises a navigation system configured to track a pose of a marker and identify the marker; a processor; and a memory storing data for processing by the processor, the data, when processed, causing the processor to: receive a first image from a surgical plan; obtain, from the navigation system, pose information describing the pose of the maker and a marker identification of the marker; identify the bone mount based on the marker identification; receive image data of a second image depicting an anatomical element and the bone mount; input the image data, the pose, and the bone mount into a registration model, the registration model configured to register the anatomical element to the first image based on the pose and the bone mount; and receive from the registration model, a registered anatomical element.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
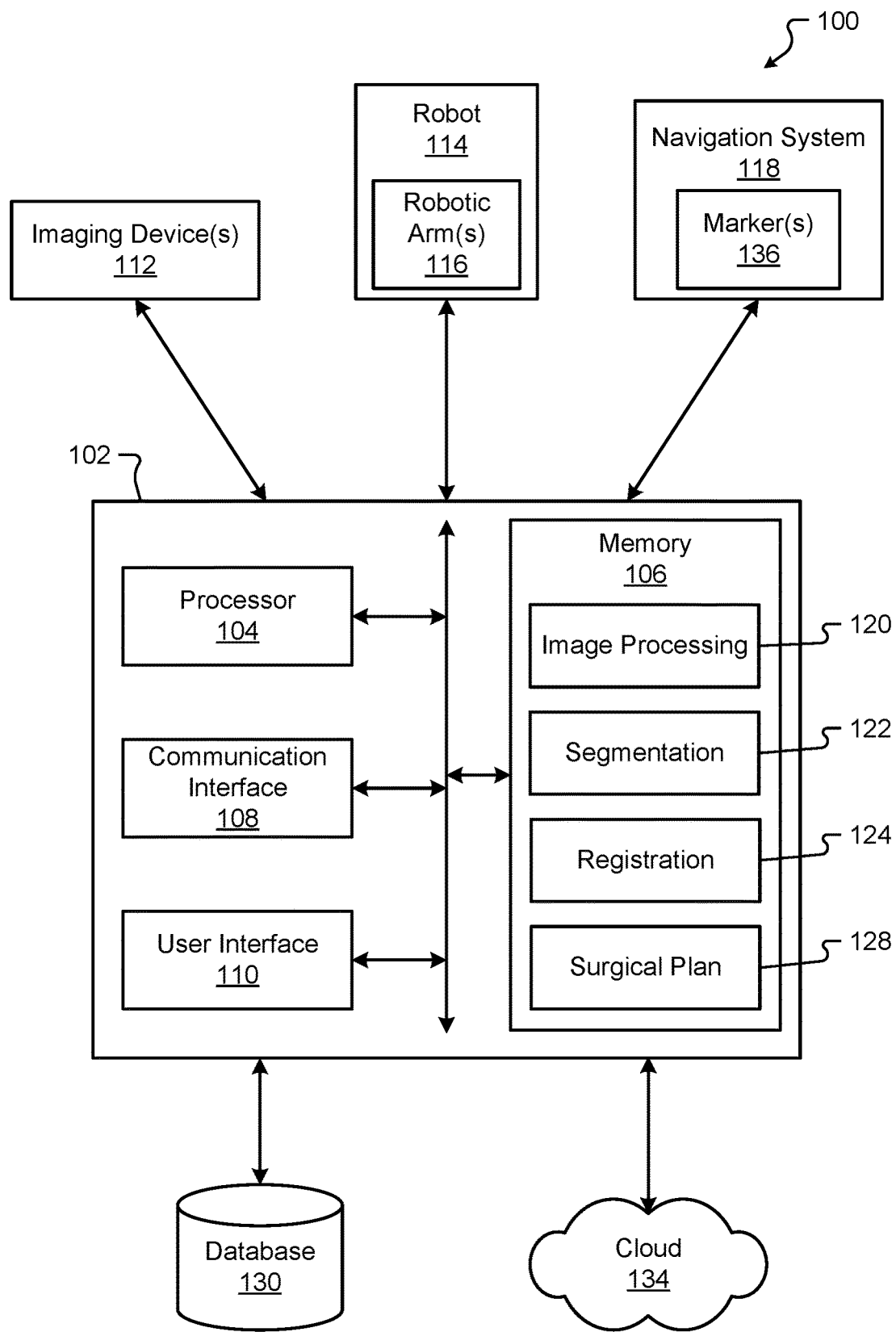
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Surgical platforms using a navigation system may rely on image-based registration such as fluoroscopy-based registration. The registration process may allow for accurate positioning of instruments and hardware based on, for example, a three-dimensional pre-operative scan of a surgical plan. However, foreign objects that do not appear in the three-dimensional pre-operative scan may cause interference with the registration process by limiting the registration algorithm's ability to recognize anatomical features within the image that may be blocked or distorted by the foreign objects. For example, a bone mount platform may interfere with the registration process. As such, some bone mount platforms are designed to be radiolucent. Such radiolucent materials are less rigid and thus, such radiolucent bone mount platforms are typically larger and less rigid than conventional bone mount platforms.

At least one embodiment according to the present disclosure provides for a navigation system that can be used to position radiopaque instruments or objects such as bone mount platforms. The navigation system can determine a pose or location of the bone mount platform and train an image processing algorithm of the registration process to ignore such objects. In some embodiments, a navigated marker may be coupled to an object such as a bone mount platform. Given the known geometry of the object (e.g., platform) components and the three-dimensional position and orientation of the object measured by the navigation system, the expected foreign artifact within the image received for registration can be identified and calculated. This can be used to teach the registration algorithm to ignore or disregard the object. Thus, radiopaque bone mounts, or other objects, may be used.

Being able to perform registration with radiopaque objects beneficially allows for the use of radiopaque materials for objects such as bone mount platforms. Such radiopaque bone mount platforms may be rigid and stable, thus increasing an accuracy of the system. Such registration also frees up space within the work volume as the footprint of the platform may be decreased. Decreasing such footprint may also beneficially increase a reachability as well as usability of the robotic arm in the surgical space.

Embodiments of the present disclosure provide technical solutions to one or more of the problems of (1) enabling a registration process with radiopaque objects, (2) reducing a footprint of objects and/or components in a surgical space, (3) increasing an accuracy of a navigation system, and (4) reducing an overall operating time by reducing registration failures.

Turning first to FIG. 1, a block diagram of a system 100 according to at least one embodiment of the present disclosure is shown. The system 100 may be used to register one or more anatomical elements and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400, 500, 600, and 700 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable image processing 120, segmentation 122, and/or registration 124.

The image processing 120 enables the processor 104 to process image data of an image (received from, for example, the imaging device 112, an imaging device of the navigation system 118, or any imaging device, etc.) for the purpose of, for example, identifying one or more anatomical elements and/or objects depicted in the image data. The image processing 120 may, in some embodiments, use information about an object (e.g., pose information of the object, an object identification identifying the object, dimensions of the object, etc.) to identify the object. The object may be, for example, a bone mount platform, a surgical instrument, a surgical implant, and/or a surgical tool. The anatomical element may be, for example, any soft tissue and/or hard tissue (e.g., bone). The information may comprise, for example, identification of anatomical element(s) and/or object(s), a boundary between an anatomical element and an object, a boundary of hard tissue and/or soft tissue, etc. The image processing 120 may, for example, identify the anatomical element and the object, and/or a boundary between the anatomical element and the object by determining a difference in or contrast between colors or grayscales of image pixels. For example, a boundary between the anatomical element and the object may be identified as a contrast between lighter pixels and darker pixels. The imaging processing 120 may also use segmentation 122, as described below.

The object(s) and/or anatomical element(s) identified from the image processing 120 may enable the registration 124 and the registration model 214 to disregard interference cause by the object and to register the anatomical element to, for example, a preoperative image, as will described in more detail below.

The segmentation 122 enables the processor 104 to process image data of an image (received from, for example, the imaging device 112, an imaging device of the navigation system 118, or any imaging device) for the purpose of, for example, identifying individual objects and/or anatomical elements in the image data. The segmentation 122 may enable the processor 104 to identify a boundary of an object or an anatomical element by using, for example, feature recognition. For example, the segmentation 122 may enable the processor 104 to identify a vertebra in the image data. In other instances, the segmentation 122 may enable the processor 104 to identify a boundary of an object or an anatomical element by determining a difference in or contrast between colors or grayscales of image pixels. The object(s) and/or anatomical element(s) identified from the segmentation 122 may also enable the registration 124 and the registration model 214 to disregard interference cause by the object and to register the anatomical element, as will described in more detail below.

The registration 124 enables the processor 104 to process the identified anatomical element(s) and identified object(s) obtained from the image processing 120 and/or the segmentation 122 to register the identified anatomical elements depicted in the image data, regardless of interference from one or more objects also depicting in the image data. It will be appreciated that though the image processing 120, the segmentation 122, and the registration 124 are described separately, that the image processing 120 and/or the segmentation 122 may be part of or a step of the registration 124. For example, registering the one or more anatomical elements may comprise using the image processing 120 and/or the segmentation 122 to identify one or more anatomical elements and/or one or more objects depicted in the image data.

The content, if provided as instructions, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The memory 106 may also store a surgical plan 128. The surgical plan 128 may comprise, for example, one or more steps for performing a surgical procedure. In some embodiments, the surgical procedure may be, for example, a spinal procedure (e.g., a spinal alignment, installing implants, osteotomy, fusion, and/or any other spinal procedure) to correct a spinal deformity. The surgical plan 128 may also comprise one or more preoperative images of a patient anatomy. The one or more preoperative images may be two-dimensional or a three-dimensional representation of the patient anatomy. The surgical plan 128 may also be stored in the database 130.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.), other aspects of patient anatomy, navigation markers such as marker(s) 136, and/or object(s) to yield image data (e.g., image data depicting or corresponding to a bone, veins, tissue, an object, a marker, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. In other examples, the image data may also comprise data corresponding to an object or a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a two-dimensional image or a three-dimensional image (e.g., a three-dimensional representation) to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position a component such as, for example, the imaging device 112 at one or more precise position(s) and orientation(s), and/or to return the imaging device 112 to the same position(s) and orientation(s) at a later point in time. The robot 114 may also be configured to position an object such as, for example, a surgical implant or a bone mount platform. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In such embodiments, each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers 136 (e.g., navigation markers) may be placed on the robot 114 (including, e.g., on the robotic arm 116), the imaging device 112, an object such as an object 500 (shown in FIG. 5) or any other object in the surgical space. The marker 136 may comprise one or more active markers, one or more passive markers, or a combination of active and passive markers. The marker 136 be, for example, light emitting diodes, infrared light emitting diodes, reflective markers, or the like. The marker 136 may be tracked by the navigation system 118, and the results of the tracking may be used by the robot 114 and/or by an operator of the system 100 or any component thereof. The navigation system 118 may also be configured to obtain pose information describing a pose of the marker 136 and a marker identification of the marker 136, which may be used to determine a correlating pose and identification of an object to which the marker 136 is coupled to.

In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robot 114, robotic arm 116, an object, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans such as the surgical plan 128 (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may also store marker identification information for each of a plurality of markers and corresponding object identification information for each of an associated plurality of objects. In some embodiments, the database 130 may also store dimensions (e.g., size, shape, volume, surface(s), mass, height, width, length, etc.) of each object. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 400, 500, 600, and 700 described herein. The system 100 or similar systems may also be used for other purposes.

Figure 2:
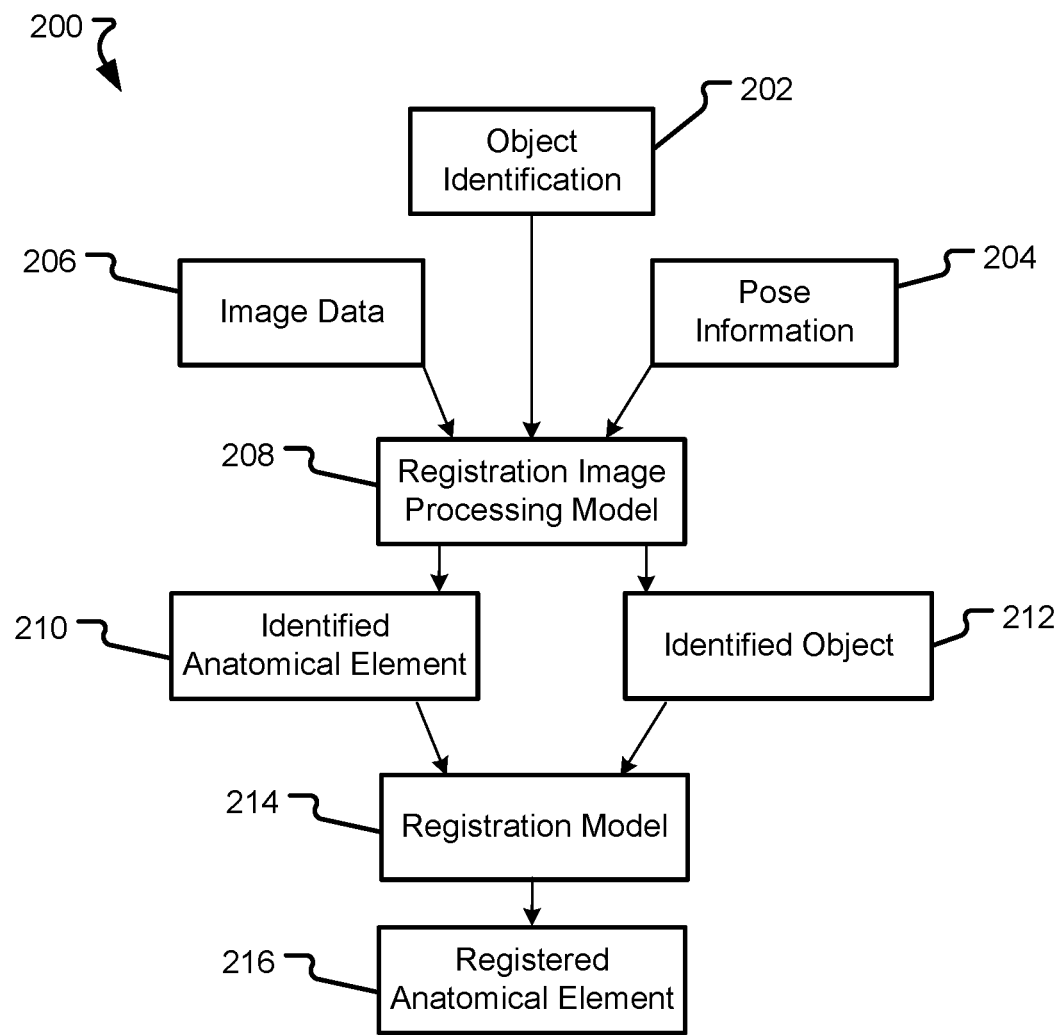
FIG. 2 is a flowchart according to at least one embodiment of the present disclosure.

Turning to FIG. 2, an example of a model architecture 200 that supports methods and systems (e.g., Artificial Intelligence (AI)-based methods and/or system) for processing image data and registering one or more anatomical elements is shown.

Image data 206, an object identification 202, and/or pose information 204 of the object may be used by a processor such as the processor 104 as input for a registration image processing model 208. It will be appreciated that the input may not include the object identification 202 and/or the pose information 204. The registration image processing model 208 may output an identified anatomical element 210 and/or an identified object 212. In some embodiments, the image data 206 may be received from an imaging device such as the imaging 112, an imaging device of a navigation system such as the navigation system 118, or any other imaging device or component of a system such as the system 100. The pose information 204 of the object may be determined from pose information of a marker such as the marker 136 obtained from a navigation system such as the navigation system 118 (as will be described in FIG. 6). It will be appreciated that in some instances, the image data may depict a marker such as the marker 136 and the image processing model 208 may process the image data to output pose information of the marker 136 (which may then be used, for example, to determine the pose information of the object). The pose information may correspond to computer-encoded data that described a pose of an object. For example, the pose information, in some embodiments, may comprise coordinates and/or an orientation of the object. In other examples, the pose information may comprise, for example, a matrix that describes the pose of the object. It will be appreciated that the pose information may be encoded in any number of ways and may include, for example, a description of a location of the object in a reference space, a vector (e.g., a three-element vector), or a matrix.

The registration image processing model 208 may use the image processing 120 and/or the segmentation 122 previously described to identify one or more objects and/or anatomical elements. For example, the image processing 120 may be configured to identify the anatomical element and the object, and/or a boundary between the anatomical element and the object by determining a difference in or contrast between colors or grayscales of image pixels. For example, a boundary between the anatomical element and the object may be identified as a contrast between lighter pixels and darker pixels. In another example, the segmentation 122 may be configured to segment one or more objects and/or anatomical elements from the image data 206 to yield one or more identified anatomical elements 210 and/or identified objects 212. Segmenting the one or more objects and/or anatomical elements from the image data 206 when the image data comprises a three-dimensional representation of the patient anatomy may comprise identifying a boundary of one or more objects and/or anatomical elements and forming a separate three-dimensional representation of the one or more objects and/or anatomical elements. In some embodiments, identifying the boundary may comprise identifying adjacent sets of pixels having a large enough contrast to represent a border of an anatomical element depicted therein. In other embodiments, feature recognition may be used to identify a border of an anatomical element and/or object. For example, a contour of a vertebrae may be identified using feature recognition.

The registration image processing model 208 may also use the object identification 202 and the pose information 204 of the object to identify the object. For example, the object may be identified in the image data based on identifying a position and orientation of the object in the image data. The object identification 202 may be used to obtain information such as, for example, dimensions of the object and the dimensions and the pose of the object may be used to identify a boundary of the object in the image data.

The image processing model 208 may be trained using historical image data, historical object identifications and/or object information, and/or historical pose information. In other embodiments, the image processing model 208 may be trained using the image data 206, the object identification 202, and/or the pose information 204. In such embodiments, the image processing model 208 may be trained prior to inputting the image data 206, the object identification 202, and/or the pose information 204 into the image processing model 208 or may be trained in parallel with inputting the image data 206, the object identification 202, and/or the pose information 204 into the image processing model 208.

As previously described, the registration image processing model 208 may output an identified anatomical element 210 and/or an identified object 212. The identified anatomical element 210 and/or the identified object 212 may be used by the processor 104 as input for a registration model 214. The registration model 214 may output one or more registered anatomical elements 216. In some embodiments, the identified objects 212 may partially block or interfere with the identified anatomical element 210 of the image data 206. In such embodiments, the registration model 214 is configured to disregard the one or more objects when registering the anatomical elements. In other words, the registration model 214 may register the anatomical elements based on a portion of the anatomical element that is depicted and unobstructed by the one or more object. More specifically, in some embodiments, the registration model 214 may be configured to flag the identified object for non-use. The registration model 214 may be configured to register the one or more anatomical elements to, for example, a first image such as a preoperative image.

The registration model 214 may be trained using historical or simulated image data depicting one or more anatomical elements and one or more objects, historical identified anatomical elements, and/or historical identified objects. In other embodiments, the registration model 214 may be trained using the identified anatomical elements 210 and the identified objects 212. In such embodiments, the registration model 214 may be trained prior to inputting the identified anatomical elements 210 and the identified objects 212 into the registration model 214 or may be trained in parallel with inputting the identified anatomical elements 210 and the identified objects 212 into the registration model 214.

Figure 3:
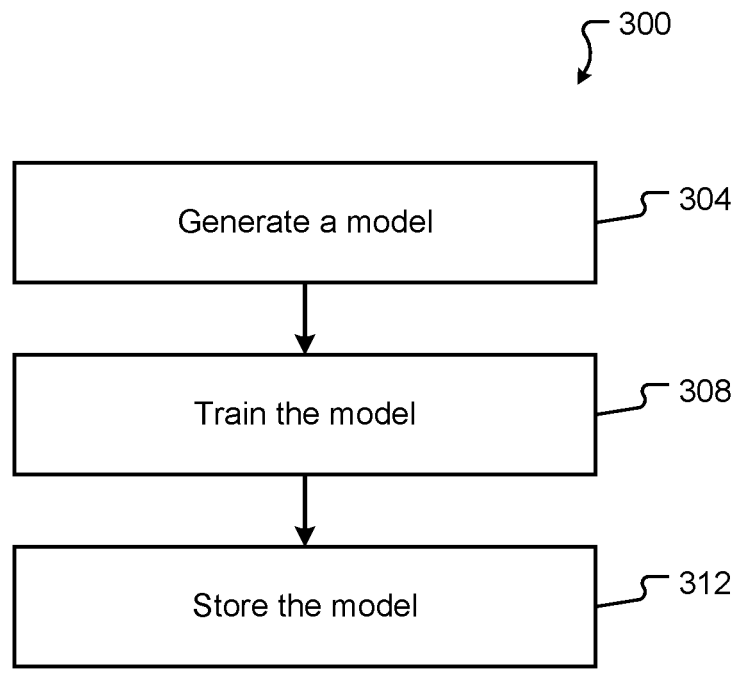
FIG. 3 is a flowchart according to at least one embodiment of the present disclosure.

FIG. 3 depicts a method 300 that may be used, for example, for generating a model is provided.

The method 300 comprises generating a model (step 304). The model may be the registration imaging processing model 208 and/or the registration model 214. A processor such as the processor 104 may generate the model. The model may be generated to facilitate and enable, for example, identification of one or more anatomical elements and/or objects depicted in image data and registration of the one or more anatomical elements.

The method 300 also comprises training the model (step 308). In embodiments where the model is trained prior to a surgical procedure, the model may be trained using historical data from a number of patients. In some embodiments, the historical data may be obtained from patients that have similar patient data to a patient on which a surgical procedure is to be performed. In other embodiments, the historical data may be obtained from any patient.

In other embodiments, the model may be trained in parallel with use of another model. Training in parallel may, in some embodiments, comprise training a model using input received during, for example, or prior to a surgical procedure, while also using a separate model to receive and act upon the same input. Such input may be specific to a patient undergoing the surgical procedure. In some instances, when the model being trained exceeds the model in use (whether in efficiency, accuracy, or otherwise), the model being trained may replace the model in use. Such parallel training may be useful, for example, in situations, where a model is continuously in use (for example, when an input (such as, for example, an image) is continuously updated) and a corresponding model may be trained in parallel for further improvements.

In some embodiments, it will be appreciated that the model trained using historical data may be initially used as a primary model at a start of a surgical procedure. A training model may also be trained in parallel with the primary model using patient-specific input until the training model is sufficiently trained. The primary model may then be replaced by the training model.

The method 300 also comprises storing the model (step 312). The model may be stored in memory such as the memory 106 and/or a database such as the database 130 for later use. In some embodiments, the model is stored in the memory when the model is sufficiently trained. The model may be sufficiently trained when the model produces an output that meets a predetermined threshold, which may be determined by, for example, a user, or may be automatically determined by a processor such as the processor 104.

The present disclosure encompasses embodiments of the method 300 that comprise more or fewer steps than those described above, and/or one or more steps that are different than the steps described above.

Figure 4:
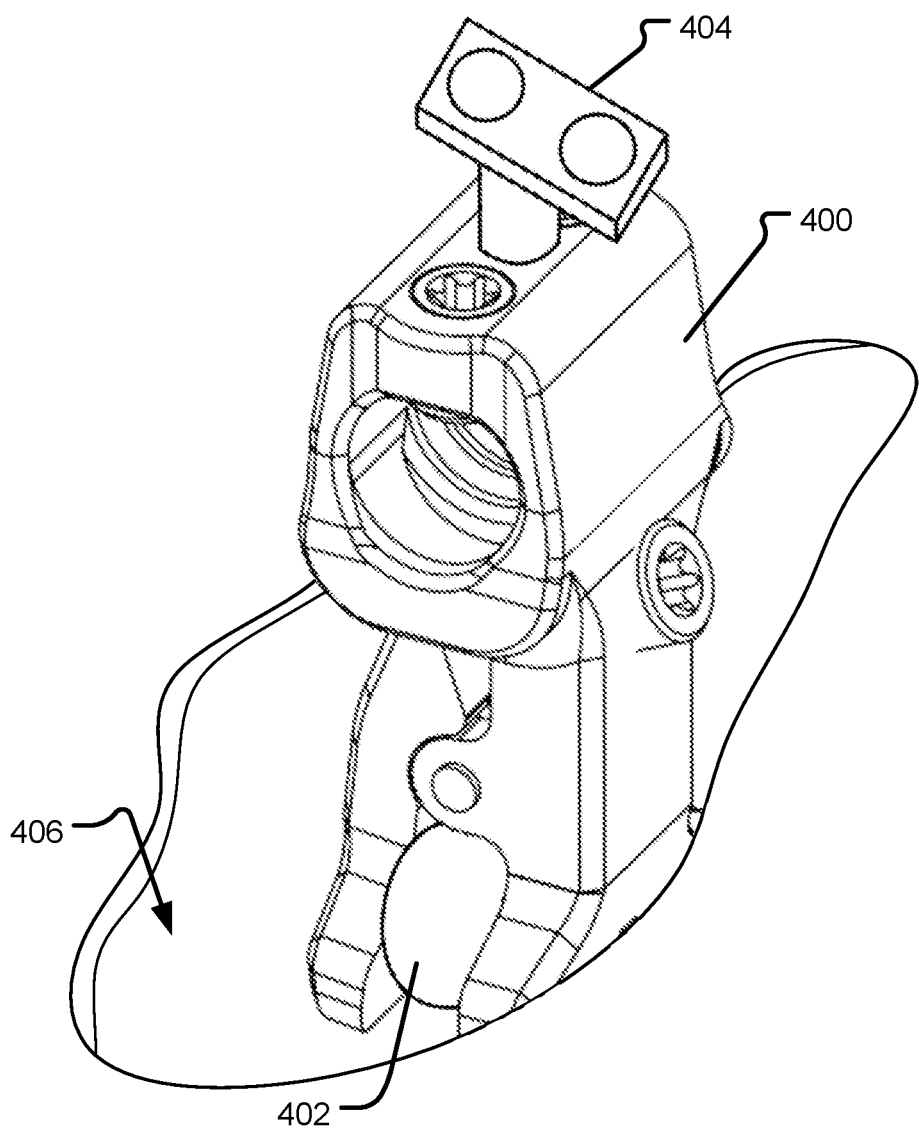
FIG. 4 is an illustration of an example marker coupled to an object according to at least one embodiment of the present disclosure.

Turning to FIG. 4, an example object 400, anatomical element 402, and a marker 404 are illustrated. The marker 404 may be the same as or similar to the marker 136. The object 400 may be a bone mount platform, as illustrated, partially inserted into an incision 406 and coupled to the anatomical element 402. It will be appreciated that the object 400 may be any object such as, for example, a surgical implant, a surgical tool, a surgical instrument, or any component in the surgical space. It will also be appreciated that the object 400 may be positioned anywhere in the surgical space. For example, the object 400 may comprise a surgical screw implanted into the anatomical element. As shown in the illustrated embodiment, the object 400 partially covers the anatomical element 402. As such, the object 400 may obstruct the anatomical element 402 in images obtained of the anatomical element 402, particularly in instances where the object 400 is radiopaque and the imaging modality uses X-Rays waves. Thus, as will be described in detail below, the marker 404 may be coupled to the object 400 and pose information and marker identification of the marker 404 may be obtained by, for example, a navigation system such as the navigation system 118. The pose information of the marker 404 may correspond to or be used to determine pose information of the object 400. The marker identification may be used to determine a corresponding object identification of the object 400 and the object identification may be used to determine information about the object 400 such as, for example, dimensions of the object 400. The object identification, the pose information of the object, and/or the dimensions of the object 400 may enable a registration model such as the registration model 214 to disregard the object 400 when registering the anatomical element 402, as described in FIGS. 5-7 below.

Figure 5:
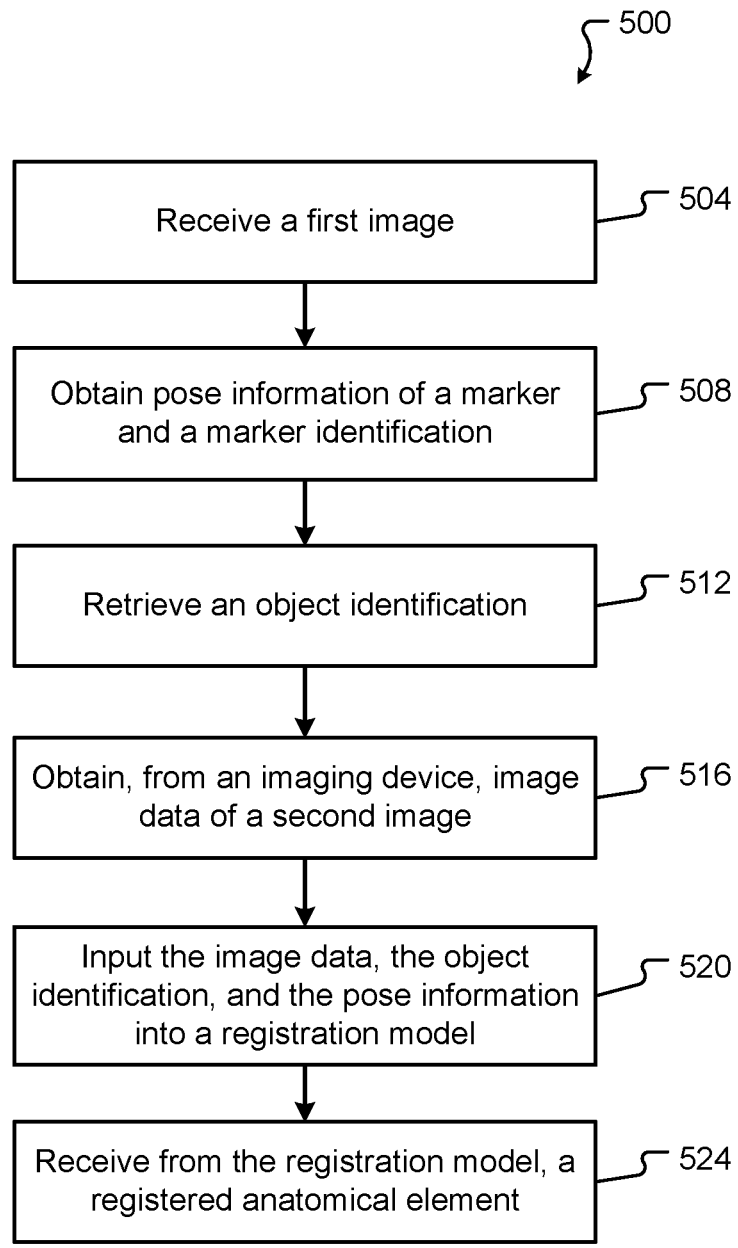
FIG. 5 is a flowchart according to at least one embodiment of the present disclosure.

FIG. 5 depicts a method 500 that may be used, for example, for registering one or more anatomical elements.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing elements stored in a memory such as the memory 106. The elements stored in memory and executed by the processor may cause the processor to execute one or more steps of a function as shown in method 500. One or more portions of a method 500 may be performed by the processor executing any of the contents of memory, such as an image processing 120, a segmentation 122, and/or a registration 124.

The method 500 comprises receiving a first image (step 504). The image may be received via a user interface such as the user interface 110, a database such as the database 130, a surgical plan such as the surgical plan 128, and/or a communication interface such as the communication interface 108 of a computing device such as the computing device 102, and may be stored in a memory such as the memory 106 of the computing device. The image may also be received from an external database or image repository (e.g., a hospital image storage system, such as a picture archiving and communication system (PACS), a health information system (HIS), and/or another system for collecting, storing, managing, and/or transmitting electronic medical records including image data), and/or via the Internet or another network. In other embodiments, the image may be received or obtained from an imaging device such as the imaging device 112, which may be any imaging device such as an MM scanner, a CT scanner, any other X-ray based imaging device, or an ultrasound imaging device. The image may also be generated by and/or uploaded to any other component of a system such as the system 100. In some embodiments, the image may be indirectly received via any other component of the system or a node of a network to which the system is connected.

The first image may be a two-dimensional image or a three-dimensional image (e.g., a three-dimensional representation) or a set of two-dimensional and/or three-dimensional images. The first image may depict a patient's anatomy or portion thereof. In some embodiments, the first image may be captured preoperatively (e.g., before surgery) and may be stored in a system (e.g., a system 100) and/or one or more components thereof (e.g., a database 130). The stored image may then be received (e.g., by a processor 104), as described above, preoperatively (e.g., before the surgery) and/or intraoperatively (e.g., during surgery). In some embodiments, the first image may depict multiple anatomical elements associated with the patient anatomy, including incidental anatomical elements (e.g., ribs or other anatomical objects on which a surgery or surgical procedure will not be performed) in addition to target anatomical elements (e.g., vertebrae or other anatomical objects on which a surgery or surgical procedure is to be performed). The first image may comprise various features corresponding to the patient's anatomy and/or anatomical elements (and/or portions thereof), including gradients corresponding to boundaries and/or contours of the various depicted anatomical elements, varying levels of intensity corresponding to varying surface textures of the various depicted anatomical elements, combinations thereof, and/or the like. The first image may depict any portion or part of patient anatomy and may include, but is in no way limited to, one or more vertebrae, ribs, lungs, soft tissues (e.g., skin, tendons, muscle fiber, etc.), a patella, a clavicle, a scapula, combinations thereof, and/or the like.

The method 500 also comprises obtaining pose information of a marker and a marker identification (step 508). The marker may be the same as or similar to the marker 136, 504 and the marker may be coupled to an object such as the object 500. In some embodiments, the pose information and the marker identification may be obtained from a navigation system such as the navigation system 118. The marker may comprise a unique pattern that the navigation may identify and use to determine the marker identification. In other embodiments, the pose information may be obtained from processing image data depicting the marker and/or the object by a processor such as the processor 104 (or a processor of the navigation system) using image processing such as the image processing 120. The pose information of the marker may correlate to or be used to determine pose information such as the pose information 204, 304 of the object. For example, a distance between the marker and the object may be predetermined and the pose of the object may be determined based on the pose of the marker and the known distance between the marker and the object.

The method 500 also comprises retrieving an object identification (step 512). The object identification may be the same as or similar to the object identification 202, 302. In some embodiments, the object identification may be received as input from, for example, the user interface. In other embodiments, the object identification may be retrieved from, for example, a database such as the database 130. The database may be configured to store marker identification for each of a plurality of markers and corresponding object identification for each of a plurality of objects. Thus, the marker identification obtained in, for example, the step 508 may be used to identify the corresponding object identification stored in the database. The object identification may be used to retrieve information about the object such as, for example, the type of object (e.g., a surgical implant, a bone mount platform, a surgical tool, etc.) and/or dimensions of the object.

The method 500 also comprises obtaining, from an imaging device, image data of a second image (step 515). The imaging device may be the same as or similar to the imaging device 112. The second image may comprise image data such as the image data 206, 306 depicting the object and one or more anatomical elements such as the anatomical elements 502. In some embodiments, the object may obstruct or obscure at least a portion of the one or more anatomical elements in the image data.

In some embodiments, the second image is obtained at a time period after the first image. For example, the first image may be obtained preoperatively and the second image may be obtained intraoperatively and prior to a start of a surgical procedure.

The method 500 also comprises inputting the image data, the object identification, and the pose information into a registration model (step 520). The registration model may be the same as or similar to the registration model 214. As previously described, the image data of the second image may depict one or more objects and one or more anatomical elements. In such image data, the one or more anatomical elements may be obstructed or partially blocked by the one or more objects. The registration model 214 may be configured to disregard the one or more objects and to register the one or more anatomical elements to the first image based on the portion of the one or more anatomical elements depicted in the image data. More specifically, the registration model may use a registration image processing model such as the registration image processing model 208. The registration image processing model may cause a processor such as the processor 104 to use image processing such as the image processing 120 and/or segmentation such as the segmentation 122 to process and/or segment the image data to identify the one or more objects and the one or more anatomical elements, as will be also described in more detail in FIGS. 6 and 7. The image processing and/or the segmentation may also use the object identification and/or the pose information to identify the one or more objects. In some embodiments, the registration model may flag the identified object(s) for non-use during a registration such as the registration 124 of the one or more anatomical elements. After the one or more anatomical elements have been registered, the registration model may output the registered anatomical element.

The method 500 also comprises receiving from the registration model, a registered anatomical element (step 524). The registered anatomical element may be the same as or similar to the registered anatomical element 216. The registered anatomical element may be registered or correlated to, for example, the first image. The registered anatomical element(s) may enable the navigation system to provide navigation during a surgical procedure.

The present disclosure encompasses embodiments of the method 500 that comprise more or fewer steps than those described above, and/or one or more steps that are different than the steps described above.

Figure 6:
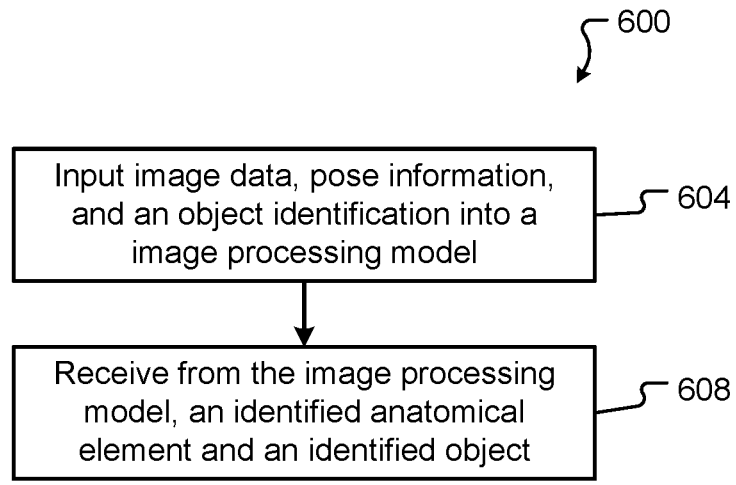
FIG. 6 is a flowchart according to at least one embodiment of the present disclosure.

FIG. 6 depicts a method 600 that may be used, for example, for processing image data using a registration image processing model.

The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 600. The at least one processor may perform the method 600 by executing elements stored in a memory such as the memory 106. The elements stored in memory and executed by the processor may cause the processor to execute one or more steps of a function as shown in method 600. One or more portions of a method 600 may be performed by the processor executing any of the contents of memory, such as an image processing 120, a segmentation 122, and/or a registration 124.

The method 600 comprises inputting image data, pose information, and an object identification into a registration image processing model (step 604). The image data may be image data of a second image obtained from, for example, the step 516 of the method 500 above; the pose information may be obtained from, for example, the step 508 of the method 500 above; and the object identification may be obtained from, for example, the step 512 of the method 500 above. The registration image processing model may be the same or similar to the registration image processing 208.

The registration image processing model may cause a processor such as the processor 104 to use image processing such as the image processing 120 and/or segmentation such as the segmentation 122 to process and/or segment the image data to identify the one or more objects and the one or more anatomical elements. In some embodiments, the image processing and/or the segmentation may use the object identification and/or the pose information to identify the one or more objects. The image processing may, for example, identify the anatomical element and the object, and/or a boundary between the anatomical element and the object by determining a difference in or contrast between colors or grayscales of image pixels. For example, a boundary between the anatomical element and the object may be identified as a contrast between lighter pixels and darker pixels. The segmentation may, for example, use feature recognition to identify a boundary of an object or an anatomical element. For example, the segmentation may enable the processor 104 to identify a vertebra in the image data.

The method 600 also comprises receiving from the registration image processing model, an identified anatomical element and an identified object (step 608). The image processing model may output, for example, an identified anatomical element such as the identified anatomical element 210 and/or an identified object such as the identified object 212. In some embodiments, the identified anatomical element and/or the identified object may be inputted to a registration model such as the registration model 214 to register the identified anatomical element. For example, the identified anatomical element and/or the identified object may be inputted to the registration model in the step 520 of the method 500 above.

The present disclosure encompasses embodiments of the method 600 that comprise more or fewer steps than those described above, and/or one or more steps that are different than the steps described above.

Figure 7:
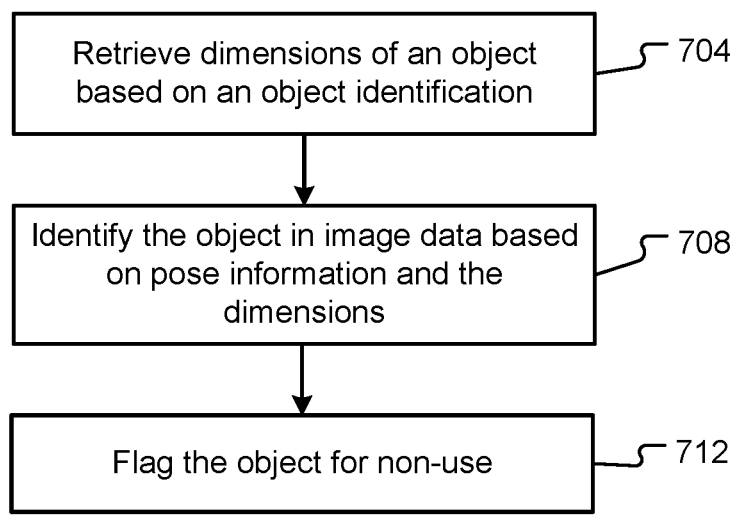
FIG. 7 is a flowchart according to at least one embodiment of the present disclosure.

FIG. 7 depicts a method 700 that may be used, for example, for identifying an object in image data. It will be appreciated that the method 700 may be used by, for example, the method 500 to identify the object in the image data.

The method 700 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 700. The at least one processor may perform the method 700 by executing elements stored in a memory such as the memory 106. The elements stored in memory and executed by the processor may cause the processor to execute one or more steps of a function as shown in method 700. One or more portions of a method 700 may be performed by the processor executing any of the contents of memory, such as an image processing 120, a segmentation 122, and/or a registration 124.

The method 700 comprises retrieving dimension of an object based on an object identification (step 704). The object may be the same as or similar to the object 500 and the object identification may be the same as or similar to the object identification 202, 302. The object identification may be determined or retrieved in the step 512 of the method 500 above. The object identification may be used to identify a corresponding dimension or set of dimensions from a database such as the database 130. As previously described, the database may store one or more dimensions of the object and a corresponding object identification. The dimensions may comprise, for example, a size, a shape, a volume, one or more surface(s), a mass, a height, a width, a length, or the like.

The method 700 also comprises identifying the object in image data based on pose information and the dimensions (step 708). The image data may be the same as or similar to the image data 206, 306 and the image data may be image data of a second image obtained from, for example, the step 516 of the method 500 above. The pose information may be obtained from, for example, the step 508 of the method 500 above and the dimensions may be dimensions of the object obtained from, for example, the step 704. Identifying the object within the image data may comprise a processor such as the processor 104 using an imaging processing such as the image processing 120 to identify pixels of the image data corresponding to the object. More specifically, the image processing may use the pose information to identify a position and orientation of the object within the image and may use the known dimensions of the object to identify the pixels corresponding to the object.

The method 700 also comprises flagging the object for non-use (step 712). The object (and more specifically, the pixels identified as representing the object) may be flagged for non-use by, for example, a registration model such as the registration model 214. By flagging the object for non-use, image data depicting an anatomical element partially obscured, blocked, or distorted by the object may still be used by the registration model to register the anatomical element. The registration model may be configured to disregard, ignore, or block the flagged object and may register the anatomical element based on at least the portion of the anatomical element depicted in the image data.

The present disclosure encompasses embodiments of the method 700 that comprise more or fewer steps than those described above, and/or one or more steps that are different than the steps described above.

As noted above, the present disclosure encompasses methods with fewer than all of the steps identified in FIGS. 4, 5, 6, and 7 (and the corresponding description of the methods 400, 500, 600, and 700), as well as methods that include additional steps beyond those identified in FIGS. 4, 5, 6, and 7 (and the corresponding description of the methods 400, 500, 600, and 700). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for registering one or more anatomical elements, the system comprising:
    an imaging device;
    a navigation system configured to track a pose of a marker coupled to an object and further configured to identify the marker;
    a registration model configured to register an anatomical element to an image;
    a processor; and
    a memory storing data for processing by the processor, the data, when processed, causing the processor to:
        receive a first image from a surgical plan;
        obtain, from the navigation system, pose information describing the pose of the marker and a marker identification of the marker;
        retrieve, from a database, an object identification based on the marker identification, wherein the database stores marker identification information for each of a plurality of markers and corresponding object identification information for each of an associated plurality of objects;
        obtain, from the imaging device, image data of a second image depicting the anatomical element and the object, the image data including a portion of the anatomical element, the anatomical element partially blocked by the object; and
        input the image data, the pose information, and the object identification into the registration model, the registration model registering the anatomical element to the first image based on the pose information and the object identification, wherein the registration model uses image processing to identify the object within the image data based on the pose information and the object identification, wherein the registration model flags the object for non-use by the registration model, wherein the registration model blocks the flagged object and does not use the image data depicting the object during registration of the anatomical element, and wherein the registration model registers the anatomical element based on the portion depicted.

2. The system of claim 1, wherein the memory stores further data for processing by the processor that, when processed, causes the processor to:

receive from the registration model, a registered anatomical element.

3. The system of claim 1, wherein the memory stores further data for processing by the processor that, when processed, causes the processor to:

input the image data, the pose information, and the object identification into an image processing model, the image processing model configured to process the image data to identify the anatomical element and the object in the image data; and receive from the image processing model, an identified anatomical element and an identified object.

4. The system of claim 1, wherein identifying the object within the image data comprises identifying pixels of the image data corresponding to the object and wherein the registration model flags the identified pixels for non-use by the registration model.

5. The system of claim 4, wherein the memory stores further data for processing by the processor that, when processed, causes the processor to:

retrieve dimensions of the object from the database based on the object identification, wherein the pixels are identified based on the pose information and the dimensions of the object.

6. The system of claim 1, wherein the marker comprises at least one of an optical marker, a magnetic marker, a light emitting diode, or an infrared light emitting diode.

7. The system of claim 1, wherein the object is at least one of a radiopaque bone mount, a surgical implant, and a surgical tool.

8. The system of claim 1, wherein the first image is a three-dimensional representation of the anatomical element and the second image is a two-dimensional representation of the anatomical element.

9. The system of claim 1, wherein the imaging device uses X-Ray imaging.

10. A system for registering one or more anatomical elements, the system comprising:

a navigation system configured to track a pose of a marker and identify the marker;

a registration model configured to register an anatomical element to an image;

a database configured to store marker identification for each of a plurality of markers and corresponding object identification for each of a plurality of objects;

a processor; and a memory storing data for processing by the processor, the data, when processed, causing the processor to:

receive a first image from a surgical plan;

obtain, from the navigation system, pose information describing the pose of the marker and a marker identification of the marker;

retrieve, from the database, an object identification based on the marker identification;

receive image data of a second image depicting the anatomical element and the object, the image data including a portion of the anatomical element, the anatomical element partially blocked by the object;

input the image data, the pose information, and the object identification into the registration model, the registration model registering the anatomical element to the first image based on the pose information and the object identification; and receive from the registration model, a registered anatomical element, wherein the registration model uses image processing to identify the object within the image data based on the pose information and the object identification, wherein the registration model flags the object for non-use by the registration model, wherein the registration model blocks the flagged object and does not use the image data depicting the object during registration of the anatomical element, and wherein the registration model registers the anatomical element based on the portion depicted.

11. The system of claim 10, wherein the memory stores further data for processing by the processor that, when processed, causes the processor to:

input the image data, the pose information, and the object identification into a segmentation model, the segmentation model configured to segment the image data to identify the anatomical element and the object in the image data; and receive from the segmentation model, an identified anatomical element and an identified object.

12. The system of claim 11, wherein the object is at least one of a radiopaque bone mount, a surgical implant, and a surgical tool.

13. The system of claim 10, wherein identifying the object within the image data comprises identifying pixels of the image data corresponding to the object and flagging the identified pixels for non-use by the registration model.

14. The system of claim 13, wherein the memory stores further data for processing by the processor that, when processed, causes the processor to:

retrieve dimensions of the object from the database based on the object identification, wherein the pixels are identified based on the pose information and the dimensions of the object.

15. The system of claim 10, wherein the marker comprises at least one of an optical marker, a magnetic marker, a light emitting diode, or an infrared light emitting diode.

16. A system for registering one or more anatomical elements, the system comprising:

a navigation system configured to track a pose of a marker and identify the marker;

a registration model configured to register an anatomical element to an image;

a processor; and a memory storing data for processing by the processor, the data, when processed, causing the processor to:

receive a first image from a surgical plan;

obtain, from the navigation system, pose information describing the pose of the marker and a marker identification of the marker;

identify a bone mount based on the marker identification;

receive image data of a second image depicting the anatomical element and the bone mount, the image data includes a portion of the anatomical element, the anatomical element partially blocked by the bone mount;

input the image data, the pose, and the bone mount into the registration model, the registration model registering the anatomical element to the first image based on the pose and the bone mount; and receive from the registration model, a registered anatomical element, wherein the registration model uses image processing to identify the bone mount within the image data based on the pose information and an object identification, wherein the registration model flags the bone mount for non-use by the registration model, wherein the registration model blocks the flagged bone mount and does not use the image data depicting the bone mount during registration of the anatomical element, and wherein the registration model registers the anatomical element based on the portion depicted.

\* \* \* \* \*